(12) United States Patent
Ghosh et al.

(10) Patent No.: US 7,390,774 B2
(45) Date of Patent: *Jun. 24, 2008

(54) ANTIBACTERIAL COMPOSITION AND METHODS OF MAKING AND USING THE SAME

(75) Inventors: Tirthankar Ghosh, Oreland, PA (US); Barry Weinstein, Dresher, PA (US)

(73) Assignee: Rohm and Haas Company, Philadelphia, PA (US)

( * ) Notice: Subject to any disclaimer, the term of this patent is extended or adjusted under 35 U.S.C. 154(b) by 403 days.

This patent is subject to a terminal disclaimer.

(21) Appl. No.: 11/070,908

(22) Filed: Mar. 3, 2005

(65) Prior Publication Data

US 2005/0227895 A1 Oct. 13, 2005

Related U.S. Application Data

(60) Provisional application No. 60/560,675, filed on Apr. 8, 2004.

(51) Int. Cl.
*C11D 3/02* (2006.01)
*C11D 3/37* (2006.01)
*A61L 2/16* (2006.01)

(52) U.S. Cl. .................. 510/199; 510/382; 510/475; 510/500; 510/508; 422/8; 422/28

(58) Field of Classification Search ............ 510/199, 510/382, 475, 500, 508; 422/8, 28
See application file for complete search history.

(56) References Cited

U.S. PATENT DOCUMENTS

| 4,104,227 | A | 8/1978 | Boessler et al. |
|---|---|---|---|
| 5,945,032 | A | 8/1999 | Breitenbach et al. |
| 6,153,210 | A | 11/2000 | Roberts et al. |
| 2003/0044447 | A1 | 3/2003 | Zanini et al. |
| 2003/0186955 | A1 | 10/2003 | Vange et al. |
| 2005/0226914 | A1 | 10/2005 | Cottrell et al. |
| 2007/0006391 | A1 | 1/2007 | Ghosh et al. |
| 2007/0082935 | A1 | 4/2007 | Chia et al. |

FOREIGN PATENT DOCUMENTS

| EP | 0331528 A | | 9/1989 |
|---|---|---|---|
| JP | 11035681 | | 2/1999 |
| JP | H11-222402 | * | 8/1999 |
| JP | 2001-97806 | | 4/2001 |
| JP | 2001 106961 | | 4/2001 |
| WO | WO 02/30204 A1 | | 4/2002 |
| WO | WO 2004/047878 A1 | | 6/2004 |

OTHER PUBLICATIONS

Miyajima, et al., "On the Complexation of Ag(I) and Cu(II) ions with poly (N-vinylimidzaole)", Reactive and Functional 38 (1998) pp. 183-195, no month given.
Journal of Inorganic Biochemistry 1997, 68(1), pp. 39-44 Jan. 3, 1997.

* cited by examiner

*Primary Examiner*—Brian P Mruk
(74) *Attorney, Agent, or Firm*—Thomas S. Deibert

(57) ABSTRACT

Antimicrobial compositions and methods of making and using the same are disclosed. The disclosed antimicrobial compositions provide persistent, broad spectrum, antimicrobial activity. The antimicrobial compositions may be used in the preparation of antimicrobial articles. The antimicrobial compositions may also be used to inhibit the growth of microorganisms by introducing those compositions onto or into an environment subject to microbial attack.

9 Claims, No Drawings

ANTIBACTERIAL COMPOSITION AND METHODS OF MAKING AND USING THE SAME

CROSS REFERENCE TO RELATED PATENT APPLICATIONS

This is a non-provisional application of prior U.S. Provisional Application Ser. No. 60/560,675 filed on Apr. 8, 2004.

The present invention relates to antibacterial compositions and to methods of making and using the same.

The constant threat of bacterial contamination and the associated repercussions on health have made antimicrobial solutions a ubiquitous part of commercial and residential cleaning and disinfection processes. Dilute aqueous detergents show no detectable reduction in bacterial levels on surfaces amenable to bacterial growth and proliferation in susceptible environments, such as hospitals and in residential kitchen and bath areas. On the other hand, oxidants such as aqueous hypochlorite and phenolic compositions produce substantial reductions in bacterial levels that are relatively short-lived (3 to 6 hours). This often results in recontamination due to reuse of such surfaces, requiring frequent reapplication of disinfectant. Further, relatively high concentrations of the active agent have to be incorporated in such formulations to obtain broad spectrum disinfection. These high concentrations often have undesirable side effects such as skin and eye irritation, in addition to being potentially hazardous when in contact with food. There is therefore a need for the development of new disinfecting formulations that can provide sustained broad spectrum microbial disinfection on surfaces over prolonged periods without reapplication, even after being contacted by cleaning solutions and after surface reuse. Furthermore, it is desirable to achieve disinfecting action without toxicity problems for the user.

A number of microbicides capable of exhibiting antibacterial activity when contained in coating compositions, resin moldings, papers and binders have been proposed. Among them are inorganic microbicides.

Most inorganic microbicides are inorganic compounds on which metal ions are supported by various methods to exhibit antimicrobial activity. Examples of inorganic compounds on which the metal ions have conventionally been supported include active carbon, apatite, zeolite, and various phosphates.

Compositions containing the inorganic microbicides on which metal ions are supported frequently exhibit instabilities which cause them to discolor upon exposure to heat and/or sun light. Hence, these inorganic microbicides frequently cause the systems into which they are incorporated to undergo conspicuous changes in coloration. Accordingly, the use of these compositions is effectively limited to systems for which such conspicuous changes in coloration can be tolerated.

One method for inhibiting such discoloration is provided by Ohsumi et al. in U.S. Pat. No. 5,698,229. Ohsumi et al. disclose the combination of an inorganic compound on which silver ions are supported with a compound of the following formula:

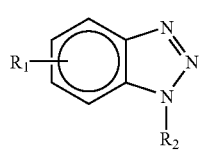

wherein $R^1$ is hydrogen or a lower alkyl group and $R^2$ is hydrogen or an alkali metal.

Another method for inhibiting such discoloration is provided by Zanini et al. in U.S. Patent Application Publication No. 2003/0044447 A1. Zanini et al. disclose antimicrobial contact lens which contain silver and a polymer comprising monomer selected from

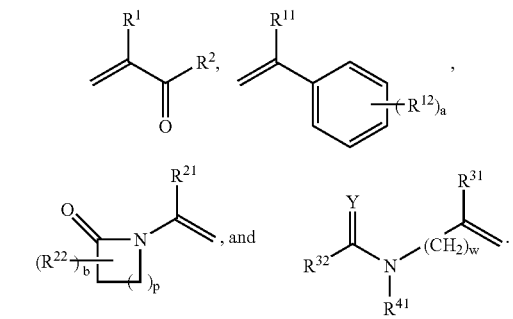

The contact lenses disclosed by Zanini et al. are asserted to exhibit clarity comparable to commercially available lenses.

Nevertheless, there remains a need for new compositions which exhibit the positive antibacterial activity of metal ions without the undesirable heat and light stability problems often associated with compositions incorporating such metal ions.

In a first aspect of the present invention, there is provided an antimicrobial composition comprising a metal complexed with a polymer, wherein the metal is selected from copper, silver, gold, tin, zinc and combinations thereof, alternatively the metal is selected from copper, silver, gold and combinations thereof, alternatively the metal is selected from copper, silver and combinations thereof, alternatively the metal is silver; and, wherein the polymer comprises monomer residues selected from residue A, residue B, residue C and mixtures thereof, with the proviso that the polymer contains no more than 99.5 wt % of monomer residues of residue B, alternatively no more than 99 wt % of monomer residues of residue B, alternatively no more than 98 wt % monomer residues of residue B, alternatively no more than 95 wt % of monomer residues of residue B, alternatively no more than 90 wt % of monomer residues of residue B;

wherein residue A is

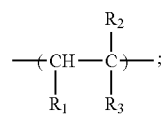

wherein residue B is

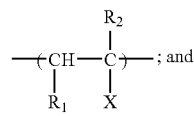

wherein residue C is

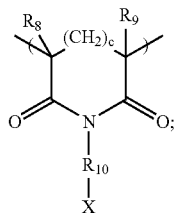

wherein

X is selected from an unsaturated or aromatic heterocycle having at least one hetero atom selected from N, O and S; alternatively X is selected from an unsaturated or aromatic heterocycle having at least one hetero N atom;

c is 0 or 1; alternatively c is 0;

$R_1$ is selected from H, $CH_3$ and $-CO_2R_4$; where $R_4$ is selected from H, $CH_3$, $C_2H_5$, a $C_3$-$C_{24}$ alkyl;

$R_2$ is selected from H, $CH_3$, $C_2H_5$, phenyl, $-CH_2CO_2R_5$ and $-CO_2R_5$; where $R_5$ is selected from (I)-(V), (I) H;

(II) 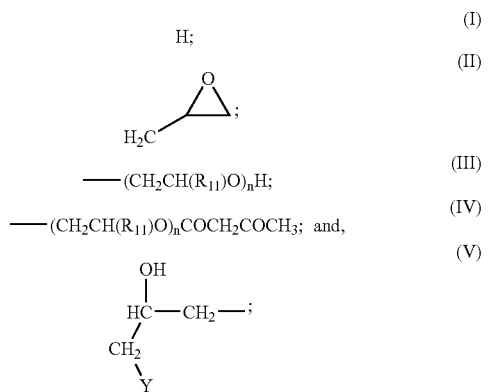

(III) $-(CH_2CH(R_{11})O)_nH$;

(IV) $-(CH_2CH(R_{11})O)_nCOCH_2COCH_3$; and, (V)

where $R_{11}$ is selected from H, methyl and phenyl; n is an integer from 1 to 20; Y is selected from OH, $SO_3Z$ and X; where Z is selected from H, sodium, potassium and $NH_4^+$; with the proviso that when the polymer contains 0 wt % of monomer residues of residue B and 0 wt % of monomer residues of residue C, $R_2$ is $-CH_2CO_2R_5$ or $-CO_2R_5$, $R_5$ is (V) and Y is X;

$R_3$ is selected from H, methyl, phenyl, sulfonated phenyl, phenol, acetate, hydroxy, a fragment O—$R_1$, where $R_1$ is as defined previously, $-CO_2R_{12}$ and $-CONR_6R_7$; where $R_6$ and $R_7$ are independently selected from H, methyl, ethyl, $C(CH_3)_2CH_2SO_3Z$, where Z is as defined previously, $C_3$-$C_8$ alkyl and a combined ring structure and $R_{12}$ is selected from H, $CH_3$, $C_2H_5$ and $C_3$-$C_{24}$ alkyl;

$R_8$ and $R_9$ are independently selected from hydrogen, methyl, ethyl and $C_3$-$C_4$ branched or straight chain alkyl; alternatively $R_8$ and $R_9$ are both hydrogen;

$R_{10}$ is selected from $C_1$-$C_8$ alkyl, $C_2$-$C_8$ alkenyl, $C_6$-$C_{10}$ unsaturated acyclic, $C_6$-$C_{10}$ cyclic, $C_6$-$C_{10}$ aromatic, $C_2$-$C_4$ alkylene oxide and poly($C_2$-$C_4$ alkylene)$_b$ oxides; where b is an integer from 2 to 20; alternatively $R_{10}$ is selected from $C_2$-$C_8$ branched and straight chain alkyl groups.

In another aspect of the present invention, there is provided an antimicrobial composition comprising a metal complexed with a polymer, wherein the metal is selected from copper, silver, gold, tin, zinc and combinations thereof, alternatively the metal is selected from copper, silver, gold and combinations thereof, alternatively the metal is selected from copper, silver and combinations thereof, alternatively the metal is silver; and, wherein the polymer comprises at least 0.5 wt % crosslinker and at least 5 wt %, alternatively at least 75 wt %, alternatively at least 80 wt %, alternatively at least 85 wt %, alternatively at least 90 wt %, alternatively at least 95 wt % of monomer residues selected from residue A, residue B, residue C and mixtures thereof; wherein residue A, residue B and residue C are as previously defined.

In another aspect of the present invention, there is provided an antimicrobial article, comprising an antimicrobial composition of the present invention.

In another aspect of the present invention, there is provided a use of an antimicrobial composition of the present invention to inhibit the growth of microorganisms in an environment by introducing the antimicrobial composition onto or into the environment.

As used herein and in the appended claims, the term "silver" refers to silver metal that is incorporated into an antimicrobial composition of the present invention. While not wanting to be bound as to the oxidation state of the silver ($Ag^0$, $Ag^{1+}$ or $Ag^{2+}$), that is incorporated into the antimicrobial composition, silver may be added to the antimicrobial composition by washing the polymer in a silver solution such as silver nitrate in deionized water ("DI"). Aside from DI, other liquid mediums can also be used such as water, aqueous buffered solutions and organic solutions such as polyethers or alcohols. Other sources of silver include but are not limited to silver acetate, silver citrate, silver iodide, silver lactate, silver picrate and silver sulfate. The concentration of silver in these solutions can vary from the concentration required to add a known quantity of silver to the antimicrobial composition to a saturated silver solution.

In another embodiment of the present invention, the antimicrobial composition contains 0.5 to 60 wt % of the metal; alternatively 0.5 to 15 wt % of the metal; alternatively 20 to 100,000 ppm metal; alternatively at least 20 ppm metal; alternatively 20 to 4,000 ppm metal; alternatively 20 to 1,500 ppm metal; alternatively 30 to 75 ppm metal; alternatively at least 50 ppm metal.

In another embodiment of the present invention, the antimicrobial composition contains silver. In one aspect of this embodiment, the antimicrobial composition contains 0.5 to 60 wt % silver; alternatively 0.5 to 15 wt % silver; alternatively 20 to 100,000 ppm silver; alternatively at least 20 ppm silver; alternatively 20 to 4,000 ppm silver; alternatively 20 to 1,500 ppm silver; alternatively 30 to 75 ppm silver; alternatively at least 50 ppm silver.

The term "alkyl" as used herein and in the appended claims includes both straight chain, branched and cyclic alkyl groups.

The term "alkenyl" as used herein and in the appended claims includes both straight chain and branched chain alkenyl groups.

Unsaturated or aromatic heterocycles suitable for use with the present invention include, for example, 5 to 7-membered heterocycles having some degree of unsaturation; aromatic heterocycles having at least one hetero atom selected from N, O and S atoms; isomers of such heterocycles and combinations thereof. In addition, suitable heterocycles may include, for example, 5 to 7-membered heterocycles that are fused together to form larger 9 to 14 membered heterocycles having at least one N, O or S atom; isomers of such heterocycles and combinations thereof. Additional heterocycles suitable for use with the present invention include 5 to 7-membered heterocycles that are fused with a carbocycle to form larger 9 to 14-membered heterocycles.

In another embodiment, the antimicrobial compositions of the present invention include a polymer comprising a heterocyclic group selected from imidazole; thiophene; pyrrole; oxazole; thiazoles and their respective isomers (e.g., thiazol-4-yl, thiazol-3-yl and thiazol-2-yl); tetrazole; pyridine; pyridazine; pyrimidine; pyrazine; azoles; indazoles; triazoles and their respective isomers (e.g., 1,2,3-triazole and 1,2,4-triazole); and combinations thereof, such as imidazole 1,2,3-triazole-1,2,4-triazole; benzotriazole; methyl-benzotriazole; benzothiazole; methylbenzothiazole; benzimidazole and methyl benzimidazole. In one aspect of this embodiment, the antimicrobial compositions of the present invention include a polymer comprising a heterocycle group selected from imidazole, benzotriazole and benzimidazole.

In another embodiment of the present invention, the antimicrobial composition comprises a heterocyclic containing monomer and a non-heterocyclic containing monomer. In one aspect of this embodiment, the ratio of the heterocyclic containing monomer to the non-heterocyclic containing monomer is 95:5 to 5:95; alternatively 80:20 to 20:80; alternatively 60:40 to 40:60. In one aspect of this embodiment, the heterocyclic containing monomer is vinylimidazole.

In another embodiment of the present invention, the antimicrobial composition comprises a heterocyclic containing monomer complexed with silver. In one aspect of this embodiment, the weight ratio of the heterocyclic containing monomer to silver is 95:5 to 5:95; alternatively 90:10 to 10:90; alternatively 80:20 to 20:80. In one aspect of this embodiment, the molar ratio of the silver to the heterocyclic containing monomer is 10:1 to 1:10; alternatively 4:1 to 1:4; alternatively 2:1 to 1:2. In one aspect of this embodiment, the heterocyclic containing monomer is vinylimidazole.

In another embodiment of the present invention, the polymer comprises 0.5 to 60 wt % cross-linker, alternatively at least 2 wt % cross-linker, alternatively at least 5 wt % cross-linker, alternatively at least 8 wt % cross-linker, alternatively at least 10 wt % cross-linker.

Cross-linkers suitable for use with the present invention include any known cross-linking material provided that the physical and chemical stability of the antimicrobial composition is substantially unaffected by inclusion of the cross-linking material. Examples of cross-linkers suitable for use with the present invention included, but are by no means limited to, di-, tri-, tetra- and higher multi-functional ethylenically unsaturated monomers such as, trivinylbenzene; divinyltoluene; divinylpyridine; divinylnaphthalene; divinylxylene; ethyleneglycol diacrylate; trimethylolpropane triacrylate; diethyleneglycol divinyl ether; trivinylcyclohexane; allyl methacrylate ("ALMA"); ethyleneglycol dimethacrylate ("EGDMA"); diethyleneglycol dimethacrylate ("DEGDMA"); propyleneglycol dimethacrylate; propyleneglycol diacrylate; trimethylolpropane trimethacrylate ("TMPTMA"); divinylbenzene ("DVB"); 2,2-dimethylpropane-1,3-diacrylate; 1,3-butyleneglycol diacrylate; 1,3-butyleneglycol dimethacrylate; 1,4-butanediol diacrylate; diethyleneglycol diacrylate; diethyleneglycol dimethacrylate; 1,6-hexanediol diacrylate; 1,6-hexanediol dimethacrylate; tripropyleneglycol diacrylate; triethyleneglycol dimethacrylate; tetraethyleneglycol diacrylate; polyethyleneglycol 200 diacrylate; tetraethyleneglycol dimethacrylate; polyethyleneglycol dimethacrylate; ethoxylated bisphenol A diacrylate; ethoxylated bisphenol A dimethacrylate; polyethyleneglycol 600 dimethacrylate; poly(butanediol) diacrylate; pentaerythritol triacrylate; trimethylolpropane triethoxy triacrylate; glycerylpropoxy triacrylate; pentaerythritol tetraacrylate; pentaerythritol tetramethacrylate; dipentaerythritol monohydroxypentaacrylate; divinyl silane; trivinyl silane; dimethyl divinyl silane; divinyl methyl silane; methyl trivinyl silane; diphenyl divinyl silane; divinyl phenyl silane; trivinyl phenyl silane; divinyl methyl phenyl silane; tetravinyl silane; dimethyl vinyl disiloxane; poly(methyl vinyl siloxane); poly (vinyl hydrosiloxane); poly (phenyl vinyl siloxane) and mixtures thereof.

In another embodiment of the present invention, the antimicrobial compositions comprise a polymer made with a cross-linker selected from allyl methacrylate (ALMA); ethyleneglycol dimethacrylate (EGDMA); diethyleneglycol dimethacrylate (DEGDMA); trimethylolpropane trimethacrylate (TMPTMA) and divinylbenzene (DVB). In one aspect of this embodiment, the antimicrobial compositions comprise a polymer made with trimethylolpropane trimethacrylate (TMPTMA).

In another embodiment of the present invention, the polymer, of which the antimicrobial composition is comprised, exhibits an average particle size of less than 200 nm; alternatively less than 50 nm; alternatively of 1 to 10 nm; alternatively less than 10 nm; alternatively of 1 to 8 nm; alternatively of less than 5 nm.

In another embodiment of the present invention, the polymer, of which the antimicrobial composition is comprised, exhibits a molecular weight of less than 500,000; alternatively of less than 100,000; alternatively of less than 50,000; alternatively of 500 to 5,000.

In another embodiment of the present invention, the antimicrobial composition is light stable. In one aspect of this embodiment, upon prolonged exposure of an antimicrobial system of the present invention to light in the visible spectrum, the individual values of Hunter L, a, b and L*a*b* (CIELAB) for the antimicrobial system exhibit a change from such exposure of less than a factor of 3; alternatively of less than a factor of 2. For a description of the Hunter Color test methods, see Billmeyer, Jr. et al., PRINCIPLES OF COLOR TECHNOLOGY, John Wiley & Sons, $2^{ED}$ (1981).

The term "prolonged exposure" as used herein and in the appended claims means an intermittent exposure period of at least 24 hours; alternatively an intermittent exposure period of at least one week; alternatively an intermittent exposure period of at least one year; alternatively an intermittent exposure period of at least two years; alternatively an intermittent exposure period of at least five years. The term "intermittent exposure period" as used herein and in the appended claims refers to a period during which the exposure to light in the visible spectrum is not constant. An example of an intermittent exposure period of 24 hours would be an ambient, outdoor light cycle from dawn to dawn.

The term "antimicrobial system" as used herein and in the appended claims includes any antimicrobial composition of the present invention, any antimicrobial article of the present invention and any environment into or onto which an antimicrobial composition of the present invention has been introduced.

The term "antimicrobial article" refers to an article that exhibits one or more of the following properties—the inhibition of the adhesion of bacteria or other microbes to the article, the inhibition of the growth of bacteria or other microbes on the article, and the killing of bacteria or other microbes on the surface of the article or in a radius extending from the article (hereinafter collectively referred to as "microbial production"). The antimicrobial articles of the present invention inhibit the microbial production by at least 25%; alternatively, the antimicrobial articles of the present invention exhibit at least a 1-log reduction ($\geqq$90% inhibition) of microbial colony forming units per mL; alternatively the antimicrobial articles of the present invention exhibit at least a 2-log reduction ($\geqq$99% inhibition) of microbial colony forming units per mL; alternatively the antimicrobial articles of the present invention exhibit at least a 6-log reduction ($\geqq$99.9% inhibition) of microbial colony forming units per mL. Such microbes include, but are not limited to, *Aureobasidium pullulans, Bacillus cereus, Bacillus thuringiensis,*

*Chaetomium globosum, Enterobacter aerogines, Escherichia coli, Gliocladtum virens, Klebsiella Pheumoniae, Legionella pneumpophila, Listeria Monocytogenes, Mycobacterium tuberculosis, Porphyromonas gingivalis, Proteus mirabilis, Proteus vulgaris, Pseudomonas aeruginosa, Saccharomyces cerevisiae, Salmonella gallinarum, Salmonella typhimurium, Staphylococcus aureus, Staphylococcus epidermidis, Streptococcus agalactiae, Streptococcus faecalis, Streptococcus mutans, Trycophyton malmsten, Vibrio parahaemolyticus, Stachybotrys, Aspergillus niger, Candida albicans* and *Penicillium funiculosum*.

In another embodiment of the present invention, the antimicrobial composition is heat stable. In one aspect of this embodiment, upon exposure of an antimicrobial system of the present invention to a temperature of at least 120° C., alternatively at least 150° C., alternatively at least 200° C., alternatively at least 300° C. for a period of at least three minutes, the individual values of Hunter L, a, b and L*a*b* (CIELAB) for the antimicrobial system exhibit a change from such exposure of less than a factor of 3; alternatively of less than a factor of 2.

The antimicrobial compositions of the present invention may be used in a variety of articles to provide antimicrobial articles exhibiting persistent, antimicrobial activity, for example, (i) medical articles including bandages, transdermal drug delivery systems, catheters, heart valves, pacemaker leads, suture rings, feeding tubes, orthopedic implants and small joint replacements; (ii) food packaging materials including paperboard cartons, plastic or paper food wraps and drink containers; (iii) food equipment including refrigerators, dishwashers, vending machines, ice making equipment, restaurant equipment and kitchen appliances; (iv) food processing equipment including cutting boards, countertops, food conveyors and process vessels; (v) transportation equipment including automobile interiors, aircraft passenger cabins, train passenger cabins and subway car interiours; (vi) personal care products including tooth brushes and mascara brushes/applicators.

The antimicrobial compositions of the present invention may be introduced onto or into a variety of environments subject to microbial attack to provide persistent, broad spectrum, antimicrobial activity. Typical environments suitable for use with the present invention include, for example, plastics, emulsions, dispersions, paints, latices, coatings, construction products (such as mastics, caulks and sealants), construction adhesives (such as ceramic adhesives, carpet backing adhesives, and laminating adhesives), industrial or consumer adhesives, photographic chemicals, printing fluids, household products (such as bathroom disinfectants or sanitizers), cosmetics and toiletries, shampoos, soaps, detergents, industrial disinfectants or sanitizers (such as cold sterilants and hard surface disinfectants), floor polishes, laundry rinse water, metalworking fluids, conveyor lubricants, hydraulic fluids, leather and leather products, textiles, textile products, wood and wood products (such as plywood, chipboard, flakeboard, laminated beams, oriented strandboard, hardboard and particleboard), petroleum processing fluids, fuel, oilfield fluids (such as injection water, fracture fluids and drilling muds), agricultural adjuvant preservation, surfactant preservation, diagnostic reagent preservation and filtration media.

In another embodiment, the antimicrobial compositions of the present invention may be deposited on the surface of a substrate to form an antimicrobial layer thereon.

In another embodiment, the antimicrobial compositions of the present invention may be used in the preparation of a polymer cast, antimicrobial article. For example, an antimicrobial composition of the present invention may be incorporated into a bulk polymerization feed stream that is subsequently cast into a steering wheel.

In another embodiment, the antimicrobial compositions of the present invention may be incorporated into a vehicle or carrier to provide a topical antiseptic or disinfectant solution or spray.

In another embodiment, the antimicrobial compositions of the present invention may be added into an environment for remediation purposes. For example, the antimicrobial compositions of the present invention may be added to bio-contaminated formulations for the remediation of such contaminated formulations.

In another embodiment, the antimicrobial compositions of the present invention may optionally include one or more antimicrobial agents, provided that the physical and chemical stability of the antimicrobial composition is substantially unaffected by such inclusion. Antimicrobial agents suitable for use with the present invention include, for example, 3-isothiazolones; 3-iodo-2-propynylbutylcarbamate; 2-bromo-2-nitropropanediol; glutaric dialdehyde; 2-n-octyl-3-isothiazolone; sodium 2-pyridinethiol-1-oxide; p-hydroxy benzoic acid alkyl ester; tris(hydroxymethyl)nitromethane; dimethylol-dimethyl-hydantion; benzisothiazolone; and 2,4, 4'-trichloro-2'-hydroxy-diphenyl ether.

In another embodiment, the antimicrobial compositions of the present invention may optionally include one or more disinfecting agents, provided that the physical and chemical stability of the antimicrobial composition is substantially unaffected by such inclusion. Disinfecting agents suitable for use with the present invention include, for example, quaternary ammonium disinfectants and phenolic disinfectants.

Some embodiments of the present invention will now be described in detail in the following Examples. All fractions and percentages set forth below in the Examples are by weight unless otherwise specified.

EXAMPLES 1-4

Preparation of Polymer Product

Polymer products were prepared using the following process:

(a) isopropanol (515 g of 99 wt %) was charged to a one liter kettle equipped with a stirrer, dropping funnel and a condenser;

(b) the contents of the kettle where heated to 80° C. with constant gentle agitation;

(c) for each of Examples 1-4, a mixture with the composition set forth in Table I was slowly added to the kettle dropwise over a two hour period, while maintaining the temperature of the kettle contents at 80° C. with constant gentle agitation;

(d) the product of (c) was maintained at 80° C. with constant gentle agitation for a period of thirty minutes;

(e) t-amyl peroxypivalate (2 g) in isopropanol (5 g of 99 wt %) was added to the product of (d);

(f) the product of (e) was maintained at 80° C. with constant gentle agitation for a period of thirty minutes;

(g) t-amyl peroxypivalate (2 g) in isopropanol (5 g of 99 wt %) was added to the product of (f);

(h) the product of (g) was maintained at 80° C. with constant gentle agitation for a period of thirty minutes;

(i) t-amyl peroxypivalate (2 g) in isopropanol (5 g of 99 wt %) was added to the product of (h);

(j) the product of (i) was maintained at 80° C. with constant gentle agitation for a period of thirty minutes;

(k) the heating source was removed and the product of (j) was allowed to cool to room temperature; and, (l) the isopropanol in Example 1 was removed from the product of (k) under vacuum to leave the polymer product.

TABLE I

| Component | Example 1 Mixture Composition | Example 2 Mixture Composition | Example 3 Mixture Composition | Example 4 Mixture Composition |
|---|---|---|---|---|
| butyl acrylate (BA) | 40 g | 40 g | 45 g | 40 g |
| vinylimidazole (VI) | 40 g | 50 g | 45 g | 0 g |
| 1-vinyl-pyrrolidone | 0 g | 0 g | 0 g | 40 g |
| acrylic acid (AA) | 10 g | 0 g | 10 g | 10 g |
| trimethylol-propane triacylate (TMPTA) | 10 g | 10 g | 0 g | 10 g |
| t-amyl peroxy-pivalate | 2 g | 2 g | 2 g | 2 g |
| isopropanol | 25 g | 25 g | 25 g | 25 g |

EXAMPLE 5

Preparation of Silver Complex with Crosslinked, Imidazole Containing Polymer

A silver complex was prepared as follows:
(a) a uniform sample of the polymer product from Example 1 (3 g) was dispersed in deionized water (17 g);
(b) ethanol (17 g of 95 wt %) was added to product of (a) with agitation;
(c) an aqueous solution of silver nitrate (0.44 g $AgNO_3$ in 5 g of deionized water) was added to product of (b) with agitation, forming a white precipitate;
(d) an aqueous ammonium hydroxide solution (4.4 g of a 5 wt % solution) was added to the product of (c) with agitation forming a product clear light yellow colored solution containing 0.53 wt % silver.

EXAMPLE 6

Preparation of Control

A non-silver containing complex was prepared as follows:
(a) a uniform sample of the polymer product from Example 1 (9 g) was dispersed in deionized water (51 g);
(b) ethanol (51 g of 95 wt %) was added to the product of (a) with agitation;
(c) an aqueous ammonium hydroxide solution (12.3 g of a 5 wt % solution) was added to the product of (b) with agitation forming a product non-silver containing complex.

EXAMPLE 7

Preparation of Silver Complex with Imidazole Containing Polymer

A silver complex was prepared as follows:
(a) a uniform sample of the polymer product from Example 3 (15 g of polymer solids in 85 g isopropanol) was mixed with deionized water (85 g) and an aqueous ammonium hydroxide solution (15 g of a 10 wt %);
(b) an aqueous silver nitrate solution (2.2 g $AgNO_3$ in 10 g or deionized water) was added to the product of (a) with agitation, forming a hazy light yellow colored solution;
(c) the product of (b) was filtered, leaving a product clear light yellow filtrate containing 0.62 wt % silver.

EXAMPLE 8

Preparation of Silver Complex with Pyrrolidone Containing Polymer

A silver complex was prepared as follows:
(a) a uniform sample of the polymer product from Example 4 (16.5 g of polymer solids in 83.5 g isopropanol) was mixed with deionized water (6.2 g);
(b) isopropanol (6 g) and an aqueous ammonium hydroxide solution (15 g of 10 wt % solution) was added to the product of (a) with agitation;
(b) an aqueous silver nitrate solution (2.2 g $AgNO_3$ in 10 g deionized water) was added to the product of (b) with agitation, forming a product colorless clear solution containing 0.63 wt % silver.

EXAMPLE 9

Preparation of Silver Complex with Crosslinked, Imidazole Containing Polymer (without Ammonia)

A silver complex was prepared as follows:
(a) a uniform sample of the polymer product from Example 1 (3.7 g) was dispersed in deionized water (6.2 g);
(b) isopropanol (6 g of 99 wt %) and 2-amino-2-methyl-propanol (1.5 g) were added to the product of (a) with agitation;
(c) an aqueous silver nitrate solution (0.7 g $AgNO_3$ in 2 g of deionized water) was added to product of (b) with agitation, forming a product light yellow solution containing 2.2 wt % silver.

EXAMPLE 10

Preparation of Silver Complex With Crosslinked, Imidazole Containing Polymer (with Ammonia)

A silver complex was prepared as follows:
(a) a uniform sample of the polymer product from Example 1 (3 g) was dispersed in deionized water (17 g);
(b) ethanol (20 g of 95 wt %) was added to the product of (a) with agitation;
(c) an aqueous silver nitrate solution (0.2 g $AgNO_3$ in 2 g of deionized water) was added to the product of (b) with agitation, forming a gummy white precipitate;
(d) an aqueous ammonium hydroxide solution (1.7 g of a 14 wt % solution) was added to the product of (c) with agitation, forming a product clear light yellow colored solution containing 0.31 wt % silver.

EXAMPLE 11

Preparation of Silver Complex with Crosslinked, Imidazole and Polyvinylpyrrolidone Containing Polymer A silver complex was prepared as follows:
(a) a uniform sample of the polymer product from Example 1 (3 g) was dispersed in deionized water (17 g);
(b) ethanol (20 g of 95 wt %) was added to the product of (a) with agitation;
(c) an aqueous silver nitrate solution (0.2 g $AgNO_3$ in 2 g of deionized water) was added to the product of (b) with agitation, forming a white precipitate;
(d) polyvinylpyrrolidone (0.4 g) was added to the product of (c) with agitation, forming a product clear light yellow colored solution containing 0.32 wt % silver.

EXAMPLE 12

Stability of Films Formed Using Products of Examples 5 and 8

The product of Example 5 was drawn on a glass slide to form a film. The product of Example 8 was similarly drawn on a separate glass slide forming clear and colorless films. The films were allowed to dry on the glass slides at room temperature overnight. The next day the glass slides with their clear and colorless films were placed on a window sill that was exposed to natural sunlight for a period of sixty (60) days. At the end of the sixty (60) day period, the film made from the product of Example 5 remained clear and colorless. The film made from the product of Example 8, however, exhibited a dark reddish black appearance.

EXAMPLES 13-16

Preparation of Silver Containing Emulsions for Treating Non-woven Fabric

Silver containing emulsions for treating non-woven fabric were prepared using the following procedure with the respective quantities listed in Table II:

(a) an acrylic polymer containing latex emulsion was mixed with deionized water;

(b) a uniform sample of polymer product solution from Example 5 was added to the product of (a) with agitation, forming a product formulation containing the concentration of silver indicated in Table II.

TABLE II

| Component | Example 13 | Example 14 | Example 15 | Example 16 |
|---|---|---|---|---|
| latex emulsion | 113.6 g[¥] | 113.6 g[¥] | 108.7 g[Ŧ] | 108.7 g[Ŧ] |
| Product of Example 5 | 6 g | 12 g | 6 g | 12 g |
| Distilled water | 880.4 g | 874.4 g | 885.3 g | 879.3 g |
| Silver concentration as (Ag+) | 27 ppm | 57 ppm | 37 ppm | 79 ppm |

[¥]Acrylic polymer containing latex commercially available from Rohm and Haas Company of Philadelphia, Pennsylvania as Rhoplex ™NW-1845K.
[Ŧ]Acrylic polymer containing latex commercially available from Rohm and Haas Company of Philadelphia, Pennsylvania as Rhoplex ™B-15j.

EXAMPLES 17-18

Preparation of Non-Silver Containing Emulsions for Treating Non-woven Fabric Non-silver containing emulsions for treating non-woven fabric were prepared using the following procedure with the respective quantities listed in Table III:

(a) an acrylic polymer containing latex emulsion was mixed with deionized water.

TABLE III

| Component | Example 17 | Example 18 |
|---|---|---|
| latex emulsion | 113.6 g[¥] | 108.7 g[Ŧ] |
| Distilled water | 867.2 g | 891.3 g |
| Silver concentration as (Ag+) | 0 ppm | 0 ppm |

[¥]Acrylic polymer containing latex commercially available from Rohm and Haas Company of Philadelphia, Pennsylvania as Rhoplex ™NW-1845K.
[Ŧ]Acrylic polymer containing latex commercially available from Rohm and Haas Company of Philadelphia, Pennsylvania as Rhoplex ™B-15j.

EXAMPLE 19

Preparation of Non-Silver Containing Emulsions for Treating Non-woven Fabric A non-silver containing emulsion for treating non-woven fabric was prepared using the following procedure:

(a) deionized water (867.2 g) was mixed with an acrylic polymer containing latex emulsion (113.6 g of Rhoplex™NW-1845K from Rohm and Haas Company of Philadelphia, Pa.);

(b) a uniform sample of polymer product solution from Example 6 (19.2 g) was added to the product of (a) with agitation, forming a product formulation containing 0 ppm of silver.

EXAMPLE 20

Disinfection Efficacy of Silver Containing Films

*Staphylococcus aureus* of ATCC 6538 strain was grown in a growth media (Nutrient Broth) and incubated at 37° C. Two sets of microscope cover glasses were inoculated with 10 μl of inoculum containing about $1 \times 10^6$ bacteria per square inch of microscope cover glass. The microscope cover glasses were then dried at 37° C. for 30 to 40 minutes. One set of microscope cover glasses was then treated by spraying thereon a sample of the product solution of Example 10 diluted to 90 ppm silver. The other set of microscope cover glasses was then treated by spraying thereon a sample of the product solution of Example 11 diluted to 90 ppm silver. Survivors were recovered by placing the microscope cover glasses in Dey-Engley Neutralizing Broth ("D/E media") for a growth-no growth determination. That is, the D/E media was observed for turbidity after 48 hours at 37° C. Turbidity being indicative of bacterial growth. The extent of continued growth on the treated microscope cover glasses was determined by viable plate counting using standard Nutrient Agar. The results of these analyses are provided in Table IV and demonstrate that the diluted product solutions from Examples 10 and 11 kill >99.99% of the treated bacteria after 24 hours of contact.

TABLE IV

| Sprayed Sample of | Log (CPU¹/ml) Reduction After | | | |
|---|---|---|---|---|
| | 10 min. | 1 hr. | 4 hr. | 24 hr. |
| Example 10 | 0 | 0 | 2 | 6 |
| Example 11 | 0 | 0 | 0 | 6 |

EXAMPLE 21

Sanitization Efficacy of Silver Containing Films

Two sets of microscope cover glasses were pre-treated with silver containing films. Specifically, a film was sprayed on from the product solution of Example 10 (diluted to 90 ppm silver with deionized water) on one set of microscope cover glasses. A film was sprayed on from the product solution of Example 11 (diluted to 90 ppm silver with deionized water) on the other set of microscope cover glasses.

*Staphylococcus aureus* of ATCC 6538 strain was grown in a growth media (Nutrient Broth) and incubated at 37° C. Two sets of pre-treated microscope cover glasses were inoculated with 10 μl of inoculum containing about $1 \times 10^6$ bacteria per square inch of microscope cover glass. The microscope cover glasses were then subjected to multiple cycles of water rinsing, abrasion and re-inoculation. Microbial survival was determined as described in Example 21 after each wash cycle. In each case, efficacy of the treated samples was compared to a control population to account for die off due to the rinsing and abrasion procedures. Tests for which the control samples showed less than $10^4$ colonies per slide subsequent to rinsing and abrasion were considered invalid. The results are provided in Table V and demonstrate that the antimicrobial activity of films drawn from diluted product solutions from Examples 10 and 11 does not diminish after 4 successive rinse/abrasion cycles.

TABLE V

| Film drawn from product solution of | Log (CPU[1]/ml) Reduction after | | | |
|---|---|---|---|---|
| | 1 cycle | 2 cycles | 3 cycles | 4 cycles |
| Example 10 | 6 | 6 | 6 | 6 |
| Example 11 | 6 | 6 | 6 | 6 |

EXAMPLE 22

Preparation of Non-woven Polyester Fabrics Containing Silver

Weighed pieces of 1 oz/yd² pointbonded polyethylene terephthalate (PET) web were pad treated by passing through a polymer product solution of one of Examples 13, 14, 15, 16, 17, 18 or 19. Excess polymer product solution was squeezed from the web by passing the web through a roller nip with a pressure of 2 bar. The samples were then dried at 149° C. for 2 minutes.

EXAMPLE 23

Silver Content Analysis of Treated Non-woven Polyester Fabrics of Example 22

The dried, treated fabric samples of Example 22 were analyzed for silver content by the following procedure, namely:
(a) an aliquot of 0.5 g of dried fabric material was weighed into a quartz beaker and covered with a Teflon® watch glass;
(b) concentrated sulfuric acid (10 ml of trace metal grade) was added to (a);
(c) the quartz beaker was then placed on a hot plate;
(d) heat was slowly increased to char the contents of the quartz beaker;
(e) the solution in the quartz beaker was then oxidized by adding nitric acid (trace metal grade) dropwise until a clear solution was produced;
(f) the clear solution of (e) was allowed to cool;
(g) the Teflon® watch glass and sides of the quartz beaker were rinsed and the rinse material was retained in the quartz beaker;
(h) the quartz beaker and its contents were heated to evaporate the solution until approximately 1 ml remained in the quartz beaker;
(i) the product of (h) was made up to 25 ml with millipore water; and
(j) a sample of the product of (i) was then analyzed using a Perkin Elmer 4300 DV Spectrometer.

A series of silver calibration standards were prepared from reference materials to bracket the concentration found in the tested samples. An analytical line used for the analysis was 328.068 nm in an axial mode. The results of the silver content analyses of the tested samples are provided in Table VI.

TABLE VI

| Sample Treated with Product Solution of | Silver Content (ppm as Ag$^+$) |
|---|---|
| Example 13 | 100 |
| Example 14 | 180 |
| Example 15 | 90 |
| Example 16 | 180 |
| Example 17 | 0 |
| Example 18 | 0 |
| Example 19 | 0 |

EXAMPLE 24

Tensile Strength of Treated Non-woven Polyester Fabrics of Example 22

The tensile strength of the treated, non-woven polyester fabrics of Example 22 was measured using an Instron in both the machine direction (MD) and the cross direction (CD) for each of the following conditions: dry, wet with water and wet in isopropanol. The wet samples were immersed in solvent for a period of 30 minutes and tested immediately upon removal from the solvent after passage through and Instron with a 2 inch gap setting, at a 12 in/min crosshead speed and a 100 lb load cell setting. The results are provided in Table VII.

TABLE VII

| Sample Treated with | Tensile Strength (in lbs) | | | | | |
|---|---|---|---|---|---|---|
| | Dry | | Water | | Isopropanol | |
| Product Solution of | MD | CD | MD | CD | MD | CD |
| Example 13 | 11.4 | 2.2 | 4.0 | 0.8 | 0.9 | 0.2 |
| Example 14 | 11.5 | 2.3 | 3.6 | 0.8 | 0.9 | 0.2 |
| Example 15 | 6.0 | 1.9 | 2.9 | 0.7 | 1.0 | 0.2 |
| Example 16 | 10.5 | 2.2 | 2.9 | 0.8 | 1.0 | 0.2 |
| Example 17 | 6.8 | 1.5 | 3.2 | 0.9 | 1.5 | 0.4 |
| Example 18 | 8.9 | 1.8 | 2.9 | 0.7 | 0.8 | 0.2 |
| Example 19 | 11.2 | 2.7 | 4.0 | 1.0 | 1.2 | 0.3 |

EXAMPLE 25

Color of the Treated Non-woven Polyester Fabrics of Example 22

The color of the treated, non-woven polyester fabrics of Example 22 was measured using a Minolta Chroma Meter CR-331 with bidirectional illumination from a pulsed xenon arc source, a 45 degree illumination angle and a 0 degree viewer angle with a 25 mm measuring area. The actual measurements were performed on 4 layers of the treated, non-woven polyester fabric samples from Example 22 using a Black Lenata card as backing. The results are provided in Table VIII. Note that the values reported in Table VIII represent the average for three individual readings take at each of three different spots on the surface of the samples.

TABLE VIII

| Sample Treated with Product Solution of | L value¥ | a value† | b value† |
|---|---|---|---|
| Example 13 | 86.68 | −3.92 | +2.96 |
| Example 14 | 86.17 | −3.92 | +2.41 |

TABLE VIII-continued

| Sample Treated with Product Solution of | L value¥ | a value‡ | b value† |
|---|---|---|---|
| Example 15 | 86.55 | −3.92 | +1.87 |
| Example 16 | 86.58 | −3.91 | +1.80 |
| Example 17 | 87.51 | −4.05 | +2.32 |
| Example 18 | 86.45 | −3.86 | +1.84 |
| Example 19 | 86.22 | −4.02 | +2.27 |

¥L = light/dark; range is 0–100, closer to 100 the more white.
‡a = red/green; range is −∞ to +∞, the more negative the more red.
†b = yellow/blue; range is −∞ to +∞, the more negative the more blue.

EXAMPLE 26

Hand of the Treated Non-woven Polyester Fabrics of Example 22

The hand of the treated, non-woven polyester fabrics of Example 22 was measured using a Thwing-Albert Handle-O-Meter Model 211-5. A specimen size of 4"×2" was used with a 5 mm gap setting and a 1" insertion. The results are reported in Table IX. The results provided represent the average value obtained for two individual specimens of each treated, non-woven polyester fabric with 4 different directional measurements.

TABLE IX

| Sample Treated with Product Solution of | Stiffness (gms) Group I | Group II |
|---|---|---|
| Example 13 | 17.6 | 17.1 |
| Example 14 | 20.4 | 18.9 |
| Example 15 | 18.6 | 17.1 |
| Example 16 | 18.7 | 19.2 |
| Example 17 | 16.7 | 15.8 |
| Example 18 | 17.0 | 16.7 |
| Example 19 | 22.0 | 21.8 |

EXAMPLE 27

Antibacterial Activity of the Treated Non-woven Polyester Fabrics of Example 22

The antibacterial activity of the treated, non-woven polyester fabrics of Example 22 was measured using a parallel streak method (AATCC Test Method 147-1988). The test samples were placed on nutrient agar inoculated with parallel streaks of the bacteria:
(a) *Staphylococcus aureus* (ATCC 6538); and
(b) *Klebsiella pneumoniae* (ATCC 4352).

Following an incubation period of 24 hours at 37° C., antibacterial activity was evaluated by measuring (in mm) the size of any clear zone of no growth (Zone of Inhibition) around each sample, and visually determining growth in the contact area. The results are provided below in Table X.

TABLE X

AATCC Test Method 147-1988

| Sample Treated with Product Solution of | Zone of Inhibition (mm)/growth in contact area | |
|---|---|---|
| | *Staphylococcus aureus* | *Klebsiella pneumoniae* |
| Example 13 | 0/NGCA¥ | 1/NGCA |
| Example 14 | 0.5/NGCA | 2/NGCA |
| Example 15 | 2/NGCA | 4/NGCA |
| Example 16 | 4/NGCA | 6/NGCA |
| Example 17 | 0/GCA£ | 0/GCA |
| Example 18 | 0/GCA | 0/GCA |
| Example 19 | 0/GCA | 0/GCA |

¥A No Growth Contact Area ("NGCA") designation is routinely used in bacterial tests. Bacterial organisms are often difficult to determine on a sample itself. Hence, the area immediately beneath the sample is examined for bacterial growth. A NGCA designation is indicated when there are not bacterial colonies detected immediately under the sample.
£A Growth Contact Area ("GCA") designation is routinely used in bacterial tests. A GCA designation is indicated when there are colonies of bacteria detected immediately under the sample.

EXAMPLE 28

Bacteriostatic Activity of the Treated Non-woven Polyester Fabrics of Example 22

The bacteriostatic activity of the treated, non-woven polyester fabrics of Example 22 was measured using the AATCC Method 100-1993. The test samples were quantitatively evaluated for bacteriostatic activity by placing 1.0 ml of a diluted culture of the test bacterial ($10^5$ organisms) in direct contact with the sterilized sample. Following a 24 hour incubation period at 37° C. and 100% relative humidity, the samples were diluted with sterile letheen broth and the number of surviving organisms were determined by the standard plate count. The percent reduction was calculated by comparison to the number of organisms recovered at zero contact time. The results of these analyses are provided in Table XI.

TABLE XI

AATCC Test Method 100-1993

Number of surviving organisms

| Sample Treated with Product Solution of | *Staphylococcus aureus* | | | *Lkebsiella pneumoniae* | | |
|---|---|---|---|---|---|---|
| | at 0 time | after 24 hrs | % reduction | at 0 time | after 24 hrs | % reduction |
| Example 13 | $2.0 \times 10^5$ | $4.0 \times 10^2$ | 99.8 | $1.6 \times 10^5$ | $3.0 \times 10^2$ | 99.8 |
| Example 14 | $2.4 \times 10^5$ | $8.0 \times 10^2$ | 99.7 | $1.3 \times 10^5$ | <100 | >99.9 |
| Example 15 | $2.9 \times 10^5$ | $5.0 \times 10^2$ | 99.8 | $1.2 \times 10^5$ | <100 | >99.9 |
| Example 16 | $3.4 \times 10^5$ | $2.3 \times 10^3$ | 99.3 | $1.4 \times 10^5$ | <100 | >99.9 |

TABLE XI-continued

AATCC Test Method 100-1993

Number of surviving organisms

| Sample Treated with Product Solution of | Staphylococcus aureus | | | Lkebsiella pneumoniae | | |
|---|---|---|---|---|---|---|
| | at 0 time | after 24 hrs | % reduction | at 0 time | after 24 hrs | % reduction |
| Example 17 | $3.1 \times 10^5$ | $1.9 \times 10^6$ | <0.01 | $1.4 \times 10^5$ | $1.2 \times 10^6$ | <0.01 |
| Example 18 | $3.4 \times 10^5$ | $1.4 \times 10^6$ | <0.01 | $1.8 \times 10^5$ | $1.6 \times 10^6$ | <0.01 |
| Example 19 | $2.6 \times 10^5$ | $1.3 \times 10^6$ | <0.01 | $1.5 \times 10^5$ | $18.1 \times 10^5$ | <0.01 |

EXAMPLE 29

Antifungal Activity of the Treated Non-woven Polyester Fabrics of Example 22

The antifungal activity of the treated, non-woven polyester fabrics of Example 22 was determined using the AATCC Method 30-1989. The test samples were placed on non-nutrient mineral salts agar and inoculated with a fungal spore suspension of *Aspergillus niger*. After a 14 day incubation period at 28° C., antifungal activity was evaluated by visually rating the degree of growth on the test samples using the following scale:

| | |
|---|---|
| No Growth | (NG) |
| Traces of Growth (less than 10% coverage) | (TG) |
| Light Growth (10 to 30% coverage) | (LG) |
| Moderate Growth (30 to 60% coverage) | (MG) |
| Heavy Stain (at least 60% coverage) | (HG) |

The results of the tests are provided in Table XII.

TABLE XII

AATCC Test Method 30-1989

| Sample Treated with Product Solution of | *Aspergillus niger* |
|---|---|
| Example 13 | NG |
| Example 14 | NG |
| Example 15 | NG |
| Example 16 | NG |
| Example 17 | LG |
| Example 18 | TG |
| Example 19 | LG |

We claim:

1. An antimicrobial composition comprising a metal complexed with a polymer, wherein the metal is selected from copper, silver, gold, tin, zinc and combinations thereof; and, wherein the polymer comprises a copolymer of a heterocyclic containing monomer and a non-heterocyclic containing monomer; wherein the ratio of the heterocyclic containing monomer to the non-heterocyclic containing monomer is 95:5 to 5:95; wherein the heterocyclic containing monomer is 1-vinylimidazole and wherein the antimicrobial composition is light stable.

2. The composition of claim 1, wherein the polymer further comprises at least 2 wt % cross-linker.

3. The composition of claim 1, wherein the polymer exhibits an average particle size of less than 10 nm.

4. The composition of claim 1, wherein the antimicrobial composition contains at least 50 ppm silver.

5. The composition of claim 1, wherein the ratio of the heterocyclic containing monomer to the non-heterocyclic containing monomer is 80:20 to 20:80.

6. The composition of claim 1, wherein the metal complexed with the polymer in the antimicrobial composition is silver.

7. An antimicrobial article, comprising an antimicrobial composition according to claim 1.

8. The composition of claim 1, wherein the polymer exhibits an average particle size of less than 200 nm.

9. The composition of claim 1, wherein the polymer comprises residues of butylacrylate and residues of 1-vinylimidazole.

* * * * *